United States Patent [19]

Manabe et al.

[11] 3,965,200

[45] June 22, 1976

[54] AROMATIC COMPOUND NITRATION CATALYZED BY AROMATIC SULFONIC ACID SUPPORTED ON SOLID CARRIER

[75] Inventors: Osamu Manabe; Takashi Kameo, both of Osaka, Japan

[73] Assignee: Osaka, Osaka, Japan

[22] Filed: July 13, 1972

[21] Appl. No.: 271,407

[30] Foreign Application Priority Data

July 13, 1971  Japan................................ 46-52241

[52] U.S. Cl............................. 260/645; 260/479 R; 260/612 D; 260/622 R; 260/646
[51] Int. Cl.[2]......................................... C07C 79/10
[58] Field of Search................. 260/645, 260/646

[56] References Cited

UNITED STATES PATENTS

| | | | |
|---|---|---|---|
| 2,948,759 | 8/1960 | Wright................................ | 260/645 |
| 3,196,186 | 7/1965 | Sogn et al.......................... | 260/645 |

*Primary Examiner*—Leland A. Sebastian
*Attorney, Agent, or Firm*—Armstrong, Nikaido & Wegner

[57] ABSTRACT

In nitrating an aromatic compound having at least one of ortho-para orientation substituents, a process which is characterized in that nitration is carried out in the presence of an aromatic sulfonic acid supported on a solid carrier in a weight ratio of 1 : 1 to 1 : 20.

7 Claims, No Drawings

AROMATIC COMPOUND NITRATION CATALYZED BY AROMATIC SULFONIC ACID SUPPORTED ON SOLID CARRIER

This invention relates to manufacture of aromatic nitro compounds, more particularly to an improved process for manufacturing aromatic mononitro compounds, whereby p-nitro compounds can be selectively produced in a large proportion by nitration of aromatic compounds having ortho-para orientation substituents.

It is well known in the art to produce aromatic nitro compounds by reacting aromatic compounds having ortho and para orientation substituents with a mixed acid of nitric acid and sulfuric acid. According to this method, however, it is unavoidable to produce ortho-nitro compounds in a much larger proportion than para-nitro compounds. For example, when toluene is nitrated by such method, the resultant product is a mixture of three isomeric mononitrotoluenes, i.e., about 60% of ortho nitrotoluene, about 5% of the meta isomer and about 35% of the para isomer. This ratio is fairly constant irrespective of the reaction conditions. As known in the art, para-nitro compounds have been most extensively used in various fields and have the greatest demand, so that the above process resulting in an over-production of ortho-nitro compounds is unprofitable for the production of para-nitro compounds.

In order to overcome the above disadvantages it has been proposed to carry out toluene nitration in the presence of a sulfonated aromatic ion exchange resin or a liquid aromatic sulfonic acid (U.S. Pat. Nos. 2,948,759 and 3,196,186). According to these methods, however, it is difficult to produce para-nitrotoluene in a para to ortho molar ratio of more than 1.0 : 1.0. The above para to ortho ratio is hereinafter referred to as "p/o ratio."

Although another process in which toluene nitration is conducted in the presence of phosphorous pentoxide has also been proposed, the yield of nitrotoluenes based on nitric acid charged is too low to carry out the process on a commercial scale and the p/o ratio is still insufficient though it increases up to about 1.1.

According to all of these conventional methods, moreover, the recovery of the catalyst used is difficult or requires complicated procedure. For example, with the method using phosphorous pentoxide, disposal of the waste acid catalyst needs cumbersome procedures and is liable to cause pollution. When ion exchange resin is used as a catalyst, it will be collapsed during the reaction, rendering the recovery thereof difficult.

One object of the invention is accordingly to provide an improved nitration process whereby the above drawbacks of the conventional processes are eliminated.

Another object of the invention is to provide a process for nitrating aromatic compounds, whereby para-nitro compounds can be obtained selectively in a much higher p/o ratio than that attained in the conventional methods.

Another object of the invention is to provide a method for manufacturing aromatic nitro compounds in a high order of yield based on nitric acid charged.

Another object of the invention if to provide a practical method for producing para-nitro compounds, in which catalyst used can be recovered without any complicated procedures.

These and other objects and advantages of the invention will be apparent from the following description.

In nitrating an aromatic compound having at least one of ortho-para orientation substituents, the present process is characterized in that nitration is carried out in the presence of an aromatic sulfonic acid supported on a solid carrier in a weight ratio of 1 : 1 to 1 : 20.

Throughout the specification a catalyst composed of a solid carrier and an aromatic sulfonic acid supported thereon is hereinafter referred to as "solid catalyst."

According to the researches of the present inventors it has been found that when an aromatic sulfonic acid supported on a solid carrier in the specific weight ratio is used as a catalyst for nitration of aromatic compounds, not only nitration reaction proceeds effectively with a high conversion of the starting aromatic compounds to mononitro compounds but also para nitration reaction occurs selectively, whereby para-nitro compounds can be obtained in a high yield with a high order of p/o ratio as compared with the conventional processes. For example, when toluene is nitrated in accordance with the present process, para-nitrotoluene can be obtained in a high p/o ratio of more than 1.3, whereas it is impossible to attain a p/o ratio of more than 1.0 when an aromatic sulfonic acid is employed as a catalyst as it is.

Moreover, the solid catalyst used in the invention can easily be recovered and employed in the reaction repeatedly by simple regeneration procedures, such as washing and drying, without conducting any complicated procedures. Aromatic sulfonic acids to be used as a catalyst in the invention are substituted or non-substituted aromatic mono- or poly-sulfonic acids. They include, for example, toluene-2,4-disulfonic acid, o-benzene disulfonic acid, m-benzene disulfonic acid, chlorobenzene-Lb 2,4-disulfonic acid, m-xylene-4,6-disulfonic acid, 5-chlorotoluene-2,4-disulfonic acid, polystyrene sulfonic acid, 1,3,5-tribromobenzene-2,4-disulfonic acid, naphthalene-1,3,6-trisulfonic acid, etc. Particularly, m-benzene disulfonic acid, toluene-2,4-disulfonic acid and chlorobenzene-2,4-disulfonic acid are preferable. The aromatic sulfonic acids can be used singly or in admixture with one another. chlorobenzene- The above aromatic sulfonic acid is employed in the form of a solid catalyst supported on a solid carrier. The carriers used in the invention are those inert under the reaction conditions of the invention and capable of supporting sulfonic acid thereon and being homogeneously dispersed in the reaction system. The carriers are preferably in the form of powders or granules passing through a 10-mesh Tyler screen. Most preferable are those passing through a 60-mesh screen. Examples of the carriers are silica gel, silica sand, asbestos fiber, pumice, glass fiber, glass bead, diatomaceous earth, powder or granules of synthetic resins such as styrene-divinyl benzene copolymer, etc. Particularly, diatomaceous earth is preferable. The aromatic sulfonic acid is supported on the solid carrier in a weight ratio between the aromatic sulfonic acid and carrier of 1 : 1 to 1 : 20. When the amount of sulfonic acid supported on the carrier is in a weight ratio of less than 1 : 20, the solid catalyst has to be used in a large amount relative to the starting aromatic compound to be nitrated if sufficient catalytic activity is to be ensured, this necessitating an apparatus of large capacity, hence impractical in commercial production. The amount of the sulfonic acid relative to the solid carrier in the ratio of larger than 1

: 1, on the other hand, will reduce not only the yield of nitro compounds but also p/o ratio of mononitro compounds produced. Thus, preferable amount of aromatic sulfonic acid relative to solid carrier is in the weight ratio between 1 : 1 and 1 : 5. The aromatic sulfonic acid can be supported on the solid carrier to produce a solid catalyst by various methods, for example, by immersing the solid carrier in the aromatic sulfonic acid itself or aqueous solution thereof for impregnation and drying the carrier impregnated with the acid.

The solid catalyst is used in the nitration process of the invention in an amount of not more than 70 weight percent, preferably 25 to 50 weight percent, based on the weight of the starting aromatic compound to be nitrated or organic solvent solution thereof. The amount of aromatic sulfonic acid per se, which is supported on the solid carrier, is usually in the range of 3 to 35 weight percent, preferably 10 to 25 weight percent, based on the weight of the starting aromatic compound to be nitrated.

The starting aromatic compounds to be nitrated in accordance with the present invention are those having at least one of ortho-para orientation substituents, such as halogen, lower alkyl, lower hydroxyalkyl, lower acetoxy alkyl, lower alkoxy, phenyl, etc. Examples of such aromatic compounds are chlorobenzene, bromobenzene, iodobenzene, toluene, ethylbenzene, xylene, cumene, biphenyl, etc. Preferable aromatic compounds particularly suitable for the present invention are toluene, chlorobenzene and orthoxylene.

Nitrating agents to be used in the invention are those conventional in the art and include, for example, fuming nitric acid, nitric acid, mixed acid of nitric acid and sulfuric acid, alkyl nitrate, nitric anhydride, nitryl halide, etc. Of these nitrating agents, fuming nitric acid and alkyl nitrate, are preferable. The nitrating agent is usually employed in an amount of 0.1 to 1 mole per acid equivalent of the aromatic sulfonic acid supported on the carrier.

In the nitration reaction of the invention inert organic solvents can be used, as required. Such solvents are those having solubility to the starting aromatic compound to be nitrated but no solubility to the sulfonic acid to be used as a catalyst. Examples of the solvents are nitrobenzene, nitromethane, chloroform, dichloroethane, tetrachloroethane and nitrated products of the starting aromatic compounds.

In accordance with the preferred mode of the process of this invention the solid catalyst is dispersed in a starting aromatic compound to be nitrated and/or a solvent therefor, and the mixture is distilled to remove water as an azeotropic mixture with the starting compound and/or the solvent, whereby a dried solid catalyst is obtained. To the dried solid catalyst is added a starting aromatic compound to be nitrated or a solution thereof dissolved in an organic solvent. A nitrating agent is added slowly with stirring. The reaction temperature varies in accordance with the kinds of aromatic compound to be nitrated, but usually is in the range of −20° to 50°C. The nitration reaction is carried out with stirring at that temperature and usually completes within 5 hours. After the reaction, the resultant mixture is filtrated to separate the solid catalyst. The solid catalyst separated is washed with the compound used as a starting material or solvent therefor, followed by drying for regeneration. The solid catalyst thus regenerated can be used repeatedly for the method of the invention. The washing is mixed with the filtrate. The mixture is washed with alkali and water and subjected to distillation to remove the unreacted starting aromatic compounds and solvent therefor, whereby mixed mononitro compounds can be obtained. The resultant mixture of mononitro compounds contains a larger amount of para-mononitro compound than that obtained by the conventional methods and can be used as it is. If desired, the mixture may be separated into each isomeric component by any conventional methods, such as fraction distillation or crystallization.

The present invention will be described in greater detail with reference to examples below, in which all parts are by weight.

EXAMPLE 1

6 parts of diatomaceous earth passing through a 80-mesh Tyler screen ("Celite 545," product of Johnes Manville Sales Corp., U.S.A.) was thoroughly mixed with a solution of 5 parts of toluene-2,4-disulfonic acid and 5 parts of water, and the mixture was thoroughly dried at 90° to 100°C. 200 parts of toluene was further added to the dried mixture and the mixture was further distilled to remove remaining water as an azeotropic mixture with toluene, whereby a mixture containing 30 parts of toluene with solid catalyst was obtained.

To the mixture was added dropwise with violent stirring 1 part of fuming nitric acid having a specific gravity of 1.52 at a temperature of −2 to 0°C over a period of 30 minutes. After completion of dropwise addition, the mixture was further stirred at the same temperature for 2 hours and then at room temperature for 2 hours. The resulting liquid reaction product was filtered. The solid catalyst was thoroughly washed with warm water and toluene, and the washing was added to the filtrate. This mixture was then fully shaken and separated into an organic layer and aqueous layer. The aqueous layer containing toluene-2,4-disulfonic acid was concentrated for use as an acid catalyst for the subsequent nitration. The organic layer was washed with 5% caustic soda solution, then with water and subjected to atmospheric distillation to remove toluene, whereby mononitrotoluene was obtained in a yield of 96% based on nitric acid. The ratio of o-, m- and p-isomers in the mononitroluene thus produced as determined by gas chromatography was 37 : 2.5 : 60.5. Thus, the p/o ratio of the mononitrotoluene was 1.63. In this reaction substantially no production of dinitrotoluene was found.

EXAMPLE 2

The solid catalyst filtered out from the reaction mixture of Example 1 was washed with 50 parts of toluene. To the washed mass was thereafter added 250 parts of fresh toluene and the mixture was distilled to remove water produced during the nitration reaction as an azeotropic mixture with toluene, whereby a dried mixture containing 30 parts of toluene with regenerated solid catalyst was obtained. The mixture was used again for the subsequent nitration conducted in the same manner as in Example 1. The nitration and regeneration of the catalyst as above were repeated 7 times. The average yield of mononitrotoluene was 88 ± 5% with average p/o ratio of 1.55.

EXAMPLE 3

In the same manner as in Example 1, toluene-2,4-disulfonic acid was adsorbed to the same diatomaceous earth as in Example 1 in various ratios shown in Table 1 below, whereby 9 kinds of dried mixtures containing 30 parts of toluene with solid catalysts were obtained. Using each dried mixture, nitration reaction was conducted in the same manner as in Example 1. The results are shown in Table 1 below.

Table 1

| Run No. | Weight ratio of acid to carrier | p/o ratio in mononitro-toluene | Yield of mono-nitrotoluene based on HNO$_3$ |
|---|---|---|---|
| 1 | 1 : 0 | 0.92 | 60 |
| 2 | 1 : 0.50 | 0.92 | 65 |
| 3 | 1 : 1.00 | 1.60 | 90 |
| 4 | 1 : 1.15 | 1.61 | 95 |
| 5 | 1 : 1.50 | 1.62 | 95 |
| 6 | 1 : 2.00 | 1.60 | 93 |
| 7 | 1 : 2.50 | 1.55 | 90 |
| 8 | 1 : 3.00 | 1.54 | 90 |
| 9 | 1 : 5.00 | 1.34 | 87 |
| 10 | 1 : 10.00 | 1.20 | 85 |

EXAMPLE 4

An aqueous solution of 5 parts of an acid catalyst specified in Table 2 below was adsorbed to 10 parts of the same diatomaceous earth as in Example 1, from which water was removed by azeotropic distillation with toluene in the same manner as in Example 1, this being followed by drying, whereby a dried mixture containing 30 parts of toluene with solid catalyst was obtained.

Using the dried mixture, nitration reaction was conducted in the same manner as in Example 1 with results shown in Table 2.

For comparison nitration reaction was also conducted in the same manner as above except that aromatic sulfonic acid was used alone without being supported on the diatomaceous earth. The results are also shown in Table 2 below.

Table 2

| Run No. | Solid catalyst Acid catalyst | Carrier | Acid cat./HNO$_3$ (Molar ratio)$^a$ | p/o ratio in mononitro-toluene | Yield of mono-nitrotoluene based on HNO$_3$ |
|---|---|---|---|---|---|
| 11 | o-Benzene disulfonic acid | D.E. | 1.3 | 1.38 | 80 |
| 12 | " | None | 1.3 | 0.96 | 77 |
| 13 | m-Benzene disulfonic acid | D.E. | 1.3 | 1.53 | 90 |
| 14 | " | None | 1.3 | 0.86 | 76 |
| 15 | Chlorobenzene disulfonic acid | D.E. | 1.3 | 1.56 | 90 |
| 16 | " | None | 1.3 | 0.90 | 75 |
| 17 | m-Xylene-4,6-disulfonic acid | D.E. | 1.3 | 1.40 | 90 |
| 18 | " | None | 1.3 | 0.93 | 77 |
| 19 | 5-Chlorotoluene-2,4-disulfonic acid | D.E. | 1.1 | 1.35 | 82 |
| 20 | " | None | 1.1 | 0.85 | 65 |
| 21 | Polystyrene sulfonic acid | D.E. | 2.0 | 1.43 | 85 |
| 22 | " | None | 2.0 | 0.90 | 50 |
| 23 | 1,3,5-tribromobenzene-2,4-disulfonic acid | D.E. | 1.3 | 1.66 | 82 |
| 24 | " | None | 1.3 | 0.89 | 40 |
| 25 | Naphthalene-1,3,6-trisulfonic acid | D.E. | 0.8 | 1.05 | 81 |
| 26 | " | None | 0.8 | 0.71 | 58 |
| 27 | 0.6 : 0.7 Molar ratio mixture of toluene-2,4-disulfonic acid and m-xylene 4,6-disulfonic acid | D.E. | 1.3 | 1.50 | 90 |
| 28 | " | None | 1.3 | 0.97 | 75 |

Note : D.E. shows the same diatomaceous earth as used in Example 1.

As apparent from Table 2, the yield of mononitrotoluene and the p/o ratio are remarkably improved when acid catalyst is used in the form of solid catalyst supported on a solid carrier, as compared with the case when acid catalyst is used alone.

EXAMPLE 5

Following the same procedure as in Example 1, nitration reaction was conducted using different kinds of carrier and varying the amounts of toluene-2,4-disulfonic acid supported on the carrier. The results are shown in Table 3 below.

Table 3

| Run No. | Carrier used | Particle size (mesh) *1 | Acid Cat./Carrier (wt/wt) | p/o ratio in mononitro-toluene | Yield of mononitro-toluene based on nitric acid (%) |
|---|---|---|---|---|---|
| 29 | Silica gel | 100 | 1 : 2 | 1.30 | 86 |
| 30 | Asbestos fiber *2 | | 1 : 3 | 1.64 | 80 |
| 31 | Silica sand | 100 | 1 : 16 | 1.60 | 92 |
| 32 | Pumice | 60 | 1 : 3 | 1.63 | 90 |
| 33 | Glass fiber | 100 | 1 : 5 | 1.42 | 80 |
| 34 | Glass bead | 80 | 1 : 10 | 1.45 | 81 |
| 35 | " | 80 | 1 : 16 | 1.53 | 82 |
| 36 | Diatomaceous earth | 80 | 1 : 1 | 1.60 | 90 |
| 37 | " | 80 | 1 : 3 | 1.55 | 90 |
| 38 | " | 80 | 1 : 4 | 1.55 | 85 |
| 39 | Resin particle *3 | 50 | 1 : 5 | 1.61 | 80 |

*1 Particle size shows the mesh of Tyler screen through which the carrier used passed.
*2 Asbestos fiber is fine powder thereof to be used for gooch crucibles by E. Merk Japan Ltd.
*3 Resin is a copolymer of styrene and divinyl benzene.

EXAMPLE 6

A dried mixture containing 30 parts of toluene and solid catalyst was prepared in the same manner as in Example 1.

Nitration reaction was conducted in the same manner as in Example 1 using an alkyl nitrate specified in Table 4 below. The results are shown in Table 4, in which are also shown the results obtained without using solid carrier.

Table 4

| Run No. | Nitrating agent | Carrier | p/o ratio in mono-nitrotoluene | Yield of mono-nitrotoluene based on nitrating agent |
|---|---|---|---|---|
| 40 | Methyl nitrate | D.E. | 1.61 | 75 |
| 41 | " | None | 1.00 | 15 |
| 42 | Tertiary-butyl nitrate | D.E. | 2.10 | 91 |
| 43 | " | None | 1.00 | 31 |

Note: D.E. shows the same diatomaceous earth used as in Example 1.

EXAMPLE 7

5 parts of diatomaceous earth the same as in Example 1 was thoroughly mixed with a solution of 5 parts of toluene-2,4-disulfonic acid and 5 parts of water and the mixture was heated at 90° to 100°C for drying. To the dried mixture was added 200 parts of an aromatic compound to be nitrated and the mixture was distilled to remove water as an azeotropic mixture with the aromatic compound added. Fresh aromatic compound to be nitrated is added to the mixture to produce a dried mixture containing a predetermined amount of the aromatic compound with a solid catalyst. Thereafter, the nitration reaction was carried out in the same manner as in Example 1. The results are shown in Table 5 below.

Table 5

| Run No. | Comp. to be nitrated Kind | Amount in dried mixture (parts) | p/o ratio in mononitro Comp. | Yield of mononitro Comp. based on HNO$_3$ |
|---|---|---|---|---|
| 44 | Ethyl benzene | 30 | 2.5 | 81 |
| 45 | Cumene | 40 | 5.4 | 75 |
| 46 | Chloro-benzene | 35 | 4.4 | 92 |
| 47 | Bromo-benzene | 45 | 3.8 | 88 |
| 48 | Iodo-benzene | 55 | 2.4 | 81 |

EXAMPLE 8

6 parts of diatomaceous earth the same as in Example 1 was thoroughly mixed with 5 parts of toluene-2,4-disulfonic acid and 10 parts of water. The mixture was dried at 100° to 105°C and further at 110°C under a pressure of 30 mm Hg for 5 hours, whereby dried solid catalyst was obtained. To the solid catalyst was added 40 parts of o-xylene and the mixture was cooled to −10°C. One part of fuming nitric acid having a specific gravity of 1.52 was added dropwise to the cooled mixture with stirring over a period of in 30 minutes. After the addition the mixture was stirred at −10°C for 3 hours and further at 20° to 25°C for 2 hours, whereby mononitroxylene was obtained with p/o ratio of 3.02. Yield was 91%.

EXAMPLE 9

5 parts of toluene-2,4-disulfonic acid was adsorbed to 6 parts of diatomaceous earth the same as in Example 1 to prepare solid catalyst. The solid catalyst was added to 300 parts of nitrobenzene and heated at a temperature not exceeding 120°C under reduced pressure to remove water as an azeotropic mixture with nitrobenzene. Thus 100 parts of nitrobenzene was distilled off with water. Thereafter, 15 parts of biphenyl was added to the dried mixture and one part of fuming nitric acid was added dropwise with stirring to the mixture cooled to 3° to 5°C in 30 minutes. The nitration reaction and post-treatment were conducted in the same manner as in Example 1, whereby mononitrobiphenyl was obtained with p/o ratio of 1.3. Yield was 87%.

What we claim is:

1. A process for the selective para mononitration of an aromatic compound containing an ortho-para directing substituent wherein said aromatic compound is chlorobenzene, bromobenzene, iodobenzene, toluene, xylene, cumene or biphenyl, said aromatic compound being subjected to nitration in the presence of an aromatic sulfonic acid supported on a solid carrier in a weight ratio of 1 : 1 to 1 : 20.

2. The process according to claim 1, in which said aromatic sulfonic acid is at least one species selected from the group consisting of toluene-2,4-disulfonic acid, o-benzene disulfonic acid, m-benzene disulfonic acid, chlorobenzene-2,4-disulfonic acid, m-xylene-4,6-disulfonic acid, 5-chlorotoluene-2,4-disulfonic acid, polystyrene sulfonic acid, 1,3,5-tribromobenzene-2,4-disulfonic acid and naphthalene-1,3,6-trisulfonic acid.

3. The process according to claim 2, in which said aromatic sulfonic acid is at least one species selected from the group consisting of m-benzene disulfonic acid, toluene-2,4-disulfonic acid and chlorobenzene-2,4-disulfonic acid.

4. The process according to claim 1, in which said solid carrier is one species selected from the group consisting of silica gel, silica sand, asbestos fiber, pumice, glass fiber, glass bead, diatomaceous earth and styrene-divinyl benzene copolymer.

5. The process according to claim 4, in which said solid carrier is diatomaceous earth.

6. The process according to claim 1, in which said aromatic sulfonic acid is supported on the solid carrier in a weight ratio of 1 : 1 to 1 : 5.

7. The process according to claim 1, in which said aromatic compound to be nitrated is one species selected from the group consisting of toluene, chlorobenzene and orthoxylene.

* * * * *